(12) United States Patent
Martin et al.

(10) Patent No.: US 12,281,318 B1
(45) Date of Patent: Apr. 22, 2025

(54) TOMATO PLANTS COMPRISING TRANSGENIC EVENT DEL/ROS1-N

(71) Applicant: Norfolk Plant Sciences Limited, Norwich (GB)

(72) Inventors: Catherine Rosemary Martin, Norwich (GB); Eugenio Butelli, Norwich (GB)

(73) Assignee: Norfolk Plant Sciences Limited, Norwich (GB)

( * ) Notice: Subject to any disclaimer, the term of this patent is extended or adjusted under 35 U.S.C. 154(b) by 0 days.

(21) Appl. No.: 18/188,694

(22) Filed: Mar. 23, 2023

Related U.S. Application Data

(60) Provisional application No. 63/324,405, filed on Mar. 28, 2022.

(51) Int. Cl.
  *C12N 15/82* (2006.01)

(52) U.S. Cl.
  CPC .................................. *C12N 15/825* (2013.01)

(58) Field of Classification Search
  None
  See application file for complete search history.

(56) References Cited

U.S. PATENT DOCUMENTS

| | | | |
|---|---|---|---|
| 8,802,925 B2 * | 8/2014 | Luo | C12N 15/825 800/317.3 |
| 9,580,725 B2 | 2/2017 | Luo et al. | |

OTHER PUBLICATIONS

Butelli et al, 2008, Nature Biotechnology, 26:1301-1308.*
Albacete et al, 2015, Journal of Experimental Botany, 66:2211-2226.*
Gerszberg et al, 2015, Plant Cell Tiss Organ Culture, 120:881-902.*
Database NCBI accession No. MN580094, "Plant binary expression vector pDEL.ROS, complete sequence", 9 pages, Dec. 15, 2019.*
Database NCBI accession No. ERX352226: HiSeq X Ten paired end sequencing, "Analysis of T-DNA insertion in transgenic Del/Ros1 tomato by genome resequencing", 1 page, Oct. 6, 2019.*
Butelli et al., "Beyond Purple Tomatoes: Combined Strategies Targeting Anthocyanins to Generate Crimson, Magenta, and Indigo Fruit", Horticulturae, 2021, 7, 327, pp. 1-14, Sep. 21, 2021.
Tzfira T, et. al., "Nuclear Import of Agrobacterium T-DNA," In: Madame Curie Bioscience Database [Internet]. Austin (TX): Landes Bioscience; 2000-2013, available on the World Wide Web at ncbi.nlm.nih.gov/books/NBK6493/.
Tomato Genome Consortium, The tomato genome sequence provides insights into fleshy fruit evolution:, Nature. May 30, 2012; vol. 485, No. 7400, pp. 635-641.
Mumm et al.., "Quality Control in the Development of Transgenic Crop Seed Products", Crop Science, vol. 41, pp. 1381-1389, Sep.-Oct. 2001.
Privalle et al., "Development of an Agricultural Biotechnology Crop Product: Testing from Discovery to Commercialization", American Chemical Society, pp. 1-9, Sep. 24, 2012.
Butelli et al., "Enrichment of tomato fruit with health-promoting anthocyanins by expression of select transcription factors", Nature Biotechnology, pp. 1-22, Oct. 2008. (including Supplementary Information, 14 pgs.).
Gheysen et al., "Illegitimate recombination in plants: a model for T-DNA integration", Genes & Development vol. 5, pp. 287-297, Nov. 22, 1990.
Mayerhofer et al., "T-DNA integration: a mode illegitimate recombination in plants", The EMBO Journal, vol. 10, No. 3, pp. 697-704, 1991.
Miguel et al., An epigenetic view of plant cells cultured in vitro: somaclonal variation and beyond, Journal of Experimental Botany, vol. 62, No. 11, pp. 3713-3725, May 26, 2011.
Mumm, "A Look at Product Development with Genetically Modified Crops: Examples from Maize", Journal of Agricultural and Food Chemistry, American Chemical Society, pp. 8254-8259, May 13, 2013.

\* cited by examiner

*Primary Examiner* — Jason Deveau Rosen
(74) *Attorney, Agent, or Firm* — Williams Mullen; David M. Saravitz

(57) ABSTRACT

The invention provides seed and plants of tomato comprising transgenic event Del/Ros1-N and progeny thereof comprising this transgenic event and uses of such seeds and plants in the production of tomato fruit and food products made tomato fruit. The invention thus relates to non-hybrid and hybrid plants, seeds, and tissue cultures of tomato comprising transgenic event Del/Ros1-N, and to methods for producing a tomato plant produced by crossing such plants with themselves or with another tomato plant, such as a plant of another genotype. The invention further relates to seeds and plants produced by such crossing. The invention further relates to parts of such plants, including the fruit and gametes of such plants.

20 Claims, 5 Drawing Sheets
Specification includes a Sequence Listing.

```
                              SEQUENCE LISTING

Sequence total quantity: 1
SEQ ID NO: 1            moltype = DNA  length = 13098
FEATURE                 Location/Qualifiers
misc_feature            1..13098
                        note = Del/Ros1 T-DNA insert and surrounding tomato genomic
                        DNA
source                  1..13098
                        mol_type = other DNA
                        organism = synthetic construct
SEQUENCE: 1
atacgtaaaa gggtcaaata ttattattaa atttttagaa aaatagatta agaaaataaa    60
tgaataagta ggtaagtcga tgacaaaata aataaggaag aagaggaaat aaataggaa    120
gaaggttgtt aaccgtaaaa gggtcaaata ttattattaa atttttctc acttacgtta    180
aaggtaagca atttcatgaa tctttaatca acatttttatg tttaaatgac gcatgagaaa   240
tgaggttgaa gaattaaaat agaacaagat taaatcggag catcaagaca aaatgtatga   300
gcaaattaaa gaggtgatgt atgtattggg cccgaatagt ttgaaattag aaagctcgca   360
attgaggtct acaggccaaa ttcgctctta gccgtacaat attactcacc ggtgcgatgc   420
cccccatcgt aggtgaaggt ggaaattaat gatccatctt gagaccacag gcccacaaca   480
gctaccagtt tcctcaaggg tccaccaaaa acgtaagcgc ttacgtacat ggtcgataag   540
aaaaggcaat ttgtagatgt tccaatacgc aaaccgcctc tccccgcgcg ttggccgatt   600
cattaatgca gctggcacga caggtttccc gactggaaag cgggcagtga gcgcaacgca   660
attaatgtga gttagctcac tcattaggca ccccaggctt tacactttat gcttccggct   720
cgtatgttgt gtggaattgt gagcggataa caatttcaca caggaaacag ctatgaccat   780
gattacgcca agctcgaaat taaccctcac taaagggaac aaaagctggt acgtaccggg   840
cccccctcg agatatcgca tgcgatcccc gtcaccggtg tgagggaact agttttgatc   900
ttgaaagatc ttttatcttt agagttaaga actctttcgt attttggtga ggtttatcc    960
tcttgagttt tggtcataga cctattcatg gctctgatac caattttaa gcgggggctt   1020
atgcggatta tttcttaaat tgataagggg ttattagggg gtatagggta taaatacaag   1080
cattccctta gcgtatagta taagtatagt agcgtacctc tatcaaattt ccatcttctt   1140
accttgcaca gggcctgcaa ccttatcctt ccttgtcttc ctccttcctt ccgtccactt   1200
catcatattt aaaccaaacc tacggggag tcaacgtaac caaccctgcc ttagcatctt    1260
ttccctaacg gcctcctgcc taagcggtac ttctagcttc gaacggcgtc tgggctccag   1320
gtttagtcgt ctcgtgtctg gtttatattc acgacaaaga tctataggga cttaggaga    1380
tctggatttt agtactggat tttggtttta ggaattagaa attttattga tagaagtatt   1440
ttacaaatac aaatacatac taagggttc ttatatgctc aacacatgag cgaaacccta    1500
taagaaccct aatttccctt atcgggaaac tactcacaca ttatttatgg agaaaataga   1560
gagagataga tttgtagaga gagactggtg atttcagcgt accgaattcc cgggttaatt   1620
tccaatttgt tgggcctcct cgaataggtt tcctaattcc ccatcctccg ttgtttctag   1680
caacttactc caccactgaa tgcagtcttc aacttcatct tgtggcgacg caacatcatt   1740
gtaaaattgc gtttgcttct cacaatctgg aatctcatca gttgttaacc ggacatttga   1800
aaattcatcg gtttttccga cttctctcgg ccaagtaacg tgcaatccgg tgaaggtccg   1860
agctcggggt cttacgatat tagtcagctt aatggttttt gtgttcataa catttttccg   1920
gcatcgttct ccatcctcgc ctaaattctt ccccacatga gtattccaaa agttcttcac   1980
gtcattagct gtccttccag gaattctacc agcaatcagc gaccatttgt tacccaacag   2040
cttatgaagc ctcacaatta ggtccacttc atctctcgaa aaccgacctc ttttgatatt   2100
tggcctcaga taattcaacc acctcagcct gcaactcttc ctacaccggt tcaaccctgc   2160
tctgtgtgga acttgatgcc atttcccttc accatactct tctatacatt gcctcaagag   2220
agtgtcttct tctttggtcc aagtacctt tctcactcca cgacaattct tttccatgga    2280
tccgcactgt gaatgattag aataatttct aaaaatccca atatgaggat gccatattta   2340
taatagaata aaataaaatg tgaacaaaga aagagataaa gtagttcact ttttgaaatc   2400
taagagagaa atgggaacaa gaaagagaca aaagtagttt caaacaaact tctcttctaa   2460
gtttagtccc tttttaaaat atgaaaccca atacgtctga ttaagaatag aaaaatatca   2520
aattttcaat ataatttata ctaatcgttt tgaattttc atactgatat agtgtacgtt    2580
tcatcataac aaccaaaacg ttgttgcttc acaacaataa tatagtagta gttaatttat   2640
tatttagtaa taagtggtcc taaaaattag ataaatatta ctatgataat ataaaaatat   2700
ttgagtcagt cctaaaaaat tatttagtat tcatacatga atcaaactga ttagttaagt   2760
gtcaacaatt ggacaagtgg catggaggtt gtaaaagaat gacataagcc aactgctatt   2820
tttatccaaa aaaagaaga caacttgaca actacatttc ttttattttt ataaatttac    2880
taatatcttc tatgcaaaat tattcggtgc ctttctaaac tttaaggttt ttatttgatg   2940
tacacctaaa ttatattta ttttaatcac tccactggac ttgttattc cttcatcata    3000
tacacctact cctattatga ctacaagttg gcaaagtaa tgatatgaat ttctacttaa    3060
ataataata gtcacctaga taattaatt taacaaaga taaatatcaa accttctcac     3120
ctaaaatttt gagcaaaact tctcactaaa acttgtggac taaacccgaa aatcttcaga   3180
aaattaatat ttagtactgg aaaagtcaga ttaaatgtct gcacaagact ttctattgtt   3240
gggaataaaa caaattaata ttggattaaa atagttgaaa tatttaggta aatgctaca    3300
tgtcatttat tcattggata ttatttctta aaatttaaaa ttcattattt aaaagttatt   3360
tttgaataag ggccgatttc gtgaaattcc ttctagatat gggtcttct agacgtaaag    3420
ttgatctatt aaattttaaa tttatcttaa attcttacaa agtaagtatt aatctttgtt   3480
tcctttacta ttcattttaca ttttgtccta tatttcgttt aaaatatgtc atatattaaa  3540
aaaaattaaa aattttactt tcttttttta cattatagct atatgacgtg acaaaaaatc   3600
aactttcaca tgcgcctagt agacttcaag ttaaagggg ataatggata ctttgcctat    3660
```

```
cttttaccat atattttaaa atccttaatt attaagtttt ccaatatctc tcaccattca  3720
ttttctccta tcatatattt taggagtcct taataattaa gtttactaat aaactttatt  3780
atatattata ggactcctca attattagtt ctctttatgt ctctcatcgt acattttcct  3840
cttgtcttat ttgttaggac acttgaaatt ttcaaaatat attttgcttt taatatatga  3900
agttgtgttt gattgtagtt tttgtaaata tatttaattt tttgaatttt tatttttctaa  3960
aagaaacata aaatttaaaa gatttaaaag tatcattaaa ctattagaaa taatatatct  4020
atgttgttaa aaatgatggt tcttaattaa ctgttttatt ataaaaatatc agataattcg  4080
ttttatttac gcaaaagtta agtgaagtaa cgaaattata aatcccatag aatattgtgt  4140
atatacttgg cacatgatga ttgtaacatc cttaattatt attaattcat cgaacctatt  4200
atttcttcat tgtctatgta catttatcct taataattcc acttcaggat ttattagttc  4260
tttggttatt ggtttaagtt tatttttacaa ccaagtgaat tgaatttgtc ctccattaat  4320
atttattgga ttaaaaaata aataaatttg ctcttatttg tagaaagatt tagactttta  4380
aaatattacg ttttctgact cttttcttat caaaatggta ctctctcact tccacaaaac  4440
ttaattacgt gaacaatatc attagggatg ggtacctatc tgtcagata tcgcatgcga  4500
tccccgtcac cggtgtgagg gaactagttt tgatcttgaa agatctttta tctttagagt  4560
taagaactct ttcgtatttt ggtgaggttt tatcctcttg agtttggtc atagacctat  4620
tcatggctct gataccaatt tttaagcggg ggcttatgcg gattatttct taaattgata  4680
aggggttatt aggggtata gggtataaat acaagcattc cctagcgta tagtataagt  4740
atagtagcgt acctctatca aatttccatc ttcttacctt gcacagggcc tgcaaccttta  4800
tccttccttg tcttcctcct tccttccgtc cacttcatca tatttaaacc aaacctacgg  4860
gggagtcaac gtaaccaacc ctgccttagc atctttttccc taacgccctc ctgcctaagc  4920
ggtacttcta gcttcgaacg gcgtctgggc tccaggttta gtcgtctcgt gtctggttta  4980
tattcacgac aaagatctat agggacttta ggagatctgg attttagtac tggatttgtg  5040
ttttaggaat tagaaatttt attgatagaa gtatttttaca aatacaaata catactaagg  5100
gtttcttata tgctcaacac atgagcgaaa ccctataaga accctaattt cccttatcgg  5160
gaaactactc acacattatt tatggagaaa atagagagag atagattttgt agagagagac  5220
tggtgatttc agcgtaccga attcccatcg aaccactttg tacaagaaag ctgggtggat  5280
ccaacttcaa gacttcatag taactttctg aagagcttgt ttgatcacac ttgctgatgc  5340
aaccttcaat cccttgcact tggctttat ggtaatggat ataattccat ctctgttgga  5400
agattgaaca gtttcggaat ccaaacttag tcgtcttacg gcttccatca cttcaagcaa  5460
tacaaactcc ttggaagaac aactcacgaa aatcaacaca tccttgtttg taatgttcac  5520
agttatatta tctgttaagg aatctttcaa tcgacctctg ctatttacgg ctccaatctt  5580
gtccgtatca gaagcctttc tcttgtttgt caacggtttc ttgacattac ttgtccttgt  5640
tgtgccataa ttatcggagg tcctctcaat ggcatcgtgc agtttagttt ttgtagttga  5700
ttcccgcccc cggccccttta ccattttgtt agattccagc tcgtcgactt tcctctcaag  5760
ccctctcaag taatctattg tatggtctag tattgatact ttgtcaacct tgccaccgga  5820
tgggactagg gatgcaagaa tcataaaccg ttcgtttatt ttctctctgc gttttctctc  5880
tgacaagacg tggtttctat caatttcatc agccgttggc tttgcaaggc agtcactgtt  5940
gccttttttgt ttaccagcat caagcctgga tgtttcatgc attctagcta cttcaaaaag  6000
tactttcttc agaaatcttt gtgaggttcc gcttcgggga acatgagtac ccgacgatcc  6060
atccttgttc caactaacga agcttgattc tctattccca tttctgaagt agggaccaag  6120
aaccaactga tgggaactct tcaaaagatt ggaaagtacc ctttgataat ggacctcatc  6180
gccttggaca cccgtgtttt ctatctgctg attgcattct gagtgctgt gcatacaatt  6240
attcgtctcc ggtgcccctt ttccatcaga aagtgggggca aaagactcta gattttcatg  6300
agtttgagat atacagtcac tagaattcat agaactattg acaattgc tgattgcatc  6360
atccatgaaa ggccagcttt tgtttgagg aacctcccca ttgatgcctt ctgccaaatt  6420
cgattcgtct atgagtaaat tgtctgcaaa ctgttatcag gagaacatat  6480
gttcgtgtct ggacaattca aaagctgatc aagatcgttt tctggtatat tagcatgttc  6540
aagcgcttca caaatgaggt cattgttgtt tgtaatactg ttggagacat agttgggaat  6600
cttgggaacg gtggcaggac tgtccaagaa tgaagtttt tatgctgga ttagattcaa  6660
atcctccggt actagctctg ttgctcccag ctcaactact ccttctgcat atggaaagca  6720
cacaactgtc tgaattgacg cactctttgc aagcaaagaa cgcgagaaaa ctttggtgtc  6780
cgcacgatga gcgttgcata gccatactgc ttgatttcgt gctaatgttc ttccaggcaa  6840
cccttggcca atattgaata tgaaagacat gcaaccaag aaaaaccact cagcatcagt  6900
gaggtcttct ggtgataatg cagcagtagg ccttttacgt tgtgtgttgg tttcaccaag  6960
tgaaagagac tcataaagtt ctctcaattg atcacttctc tgcaatccca gctgatcgg  7020
attcaattcg acagattgta cagttttcg agtttaata tctccattgt agaacccatc  7080
accccactcc aagaccctg gttgtgcaac tgaattggac cagaaaattg cataactcca  7140
ttggatactt ctaacagcaa tagcaagttg cttcctcaaa ttctcaggca ctatctttgg  7200
gttttggata ccagtagcca tggtagcctg ctttttttgta caaacttgtt tgatggggat  7260
ccgtcgacct gcaggcggcc gcgaattcac tagtgattcg ggatccgcac tgtgaatgat  7320
tagaataatt tctaaaaatc ccaatatgag gatgccatat ttataataga ataaaataaa  7380
atgtgaacaa agaaagagat aaagtagttc acttttttaa atctaagaga gaatgggaa  7440
caagaaagag acaaaagtag tttcaaacaa acttctcttc taagtttagt cccttttaa  7500
aatatgaaac ccaatacgtc tgattaagaa tagaaaaata tcaaattttc aatataattt  7560
atactaatcg ttttgaattt ttcatactga tatagtgtac gtttcatcat aacaaccaaa  7620
acgttgttgc ttcacaacaa taatatagta gtagttaatt tatttatttag taataagtgg  7680
tcctaaaaat tagataaaata ttactatgat aatataaaaa tatttgagtc agtcctaaaa  7740
aattatttag tattcataca tgaatcaaac tgattagtta agtgtcaaca attggacaag  7800
tggcatggag gttgtaaaag aatgacataa gccaactgct atttttatcc aaaaaaaaga  7860
agacaacttg acaactacat tttctttatt tttataaatt tactaatatc ttctatgcaa  7920
aattattcgg tgcctttcta aacttaagg ttttatttg atgtacacct aaattatatt  7980
ttattttaat cactccactg gacttgttta ttccttcatc atatacacct actcctatta  8040
tgactacaag ttggcaaaag taatgatatg aatttctact taataaata atagtcacct  8100
agataaaatta atttaacaaa agataaatat caaaccttct cacctaaaat tttgagcaaa  8160
acttctcact aaaactgtgt gactaaaccc gaaaatcttc agaaaattaa tatttagtac  8220
tggaaaagtc agattaaatg tctgcacaag actttctatt gttgggaata aaacaaatta  8280
atattggatt aaaatagttg aaatatttag gtaaaatgct acatgtcatt tattcattgg  8340
atattatttc ttaaaattta aaattcatta tttaaaagtt attttgaat aagggccgat  8400
```

```
ttcgtgaaat tccttctaga tatgggtctt tctagacgta aagttgatct attaaatttt   8460
aaatttatct taaattctta caaagtaagt attaatcttt gtttccttta ctattcattt   8520
acatttgtc  ctatatttcg tttaaaatat gtcatatatt aaaaaaaatt aaaaatttta   8580
cttttctttt ttacattata gctatatgac gtgacaaaaa atcaactttc acatgcgcct   8640
agtagacttc aagttaaaag gggataatgg atactttgcc tatcttttac catatatttt   8700
aaaatcctta attattaagt tttccaatat ctctcaccat tcattttctc ctatcatata   8760
ttttaggagt ccttaataat taagtttact aataaactttt attatatatt ataggactcc   8820
tcaattatta gttctcttta tgtctctcat cgtacatttt cctcttgtct tatttgttag   8880
gacacttgaa attttcaaaa tatattttgc ttttaatata tgaagttgtg tttgattgta   8940
gtttttgtaa atatatttaa ttttttgaat tttatttttc taaaagaaac ataaaattta   9000
aaagatttaa aagtatcatt aaactattag aaataatata tctatgttgt taaaaatgat   9060
ggttcttaat taactgtttt attataaaat atcagataat tcgttttatt tacgcaaaag   9120
ttaagtgaag taacgaaatt ataaatccca tagaatattg tgtatatact tggcacatga   9180
tgattgtaac atccttaatt attattaatt catcgaacct attatttctt cattgtctat   9240
gtacatttat ccttaataat tccacttcag gatttattag ttctttggtt attggtttaa   9300
gtttatttta caaccaagtg aattgaattt gtcctccatt aatatttatt ggattaaaaa   9360
ataaataaat ttgctcttat ttgtagaaag atttagactt ttaaaatatt acgttttctg   9420
actcttttct tatcaaaatt ggactctctc acttccacaa aacttaatta cgtgaacaat   9480
atcattaggg atgggtaccg agctccaatt cgccctatag tgagtcgtat tacaattcac   9540
tggccgtcgt tttacaacgt cgtgactggg aaaaccctgg cgttacccaa cttaatcgcc   9600
ttgcagcaca tccccctttc gccagctggc gtaatagcga agaggcccgc accgatcgcc   9660
cttcccaaca gttgcgcagc ctgaatggcg aatgggacgc gccctgtagc ggcgcattaa   9720
gcgcggcggg tgtggtggtt acgcgcagcg tgaccgctac acttgccaaa catccaacgt   9780
cgctttcagg gatcagcttt tgccattctc accggattca gtcgtcactc atggtgattt   9840
ctcacttgat aaccttatt ttgacgaggg gaaattaata ggttgtattg atgttgacg   9900
agtcggaatc gcagaccgat accaggatct tgccatccta tggaactgcc tcggtgagtt   9960
ttctccttca ttacagaaac ggctttttca aaaatatggt attgataatc ctgatatgaa  10020
taaattgcag tttcatttga tgctcgatga gttttttctaa tcagaattgg ttaattggtt  10080
gtaacactgg cagagcatta cgctgacttg acgggacggc ggctttgttg aataaatcga  10140
acttttgctg agttgaagga tcagatcacg catcttcccg acaacgcaga ccgttccgtg  10200
gcaaagcaaa agttcaaaat caccaactgg tccacctaca acaaagctct catcaaccgt  10260
ggctccctca ctttctggct ggatgatggg gcgattcagg cctggtatga gtcagcaaca  10320
ccttcttcac gaggcagacc tcagcgcccc ccccccctg caggtcgacc aaagcggcca  10380
tcgtgcctcc ccactcctgc agttcggggg catggatgcg cggatagccg ctgctggttt  10440
cctggatgcc gacggatttg cactgccggt agaactccgg gaggtcgtcc agcctcaggc  10500
agcagctgaa ccaactcgcg aggggatcga gccctgctg agcctcgaca tgttgtcgca  10560
aaattcgccc tggaccccgcc caacgatttg tcgtcactgt caaggttga cctgcacttc  10620
atttggggcc cacatacacc aaaaaaatgc tgcataattc tcgggcagc aagtcggtta  10680
cccgcgcc gtgctggacc gggttgaatg tgcccgtaa ctttcggtag agcggacggc  10740
caatactcaa cttcaaggaa tctcacccat gcgcgccggc ggggaaccgg agttccctc  10800
agtgagcgtt attagttcgc cgctcggtgt gtcgtagata ctagccctg gggcactttt  10860
gaaatttgaa taagatttat gtaatcagtc ttttaggttt gaccggttct gccgcttttt  10920
ttaaaattgg atttgtaata ataaacgca attgtttgtt attgtggcgc tctatcatag  10980
atgtcgctat aaacctattc agcacaatat attgttttcc ttttaatatt gtacatataa  11040
gtagtagggt acaatcagta aattgaacgg agaatattat tcataaaaat acgatagtaa  11100
cgggtgatat attcattaga atgaaccgaa accggcggta aggatctgag ctacacatgc  11160
tcaggttttt tacaacgtgc acaacagaat tgaaagcaaa tatcatgcga tcataggcgt  11220
ctcgcatatc tcattaaagc aggactctag cgaaccccag agtcccgctc agaagaactc  11280
gtcaagaagg cgatagaagg cgatgcgctg cgaatcggga gcggcgatac cgtaaagcac  11340
gaggaagcgg tcagcccatt cgccgccaag cctcttcagca atatcacggg tagccaacgc  11400
tatgtcctga tagcggtccg ccacacccag ccggccacag tcgatgaatc cagaaaagcg  11460
gccattttcc accatgatat tcggcaagca ggcatcgcca tgagtcacga cgagatcctc  11520
gccgtcgggc atgcgcgcct tgagcctggc gaacagttcg gctggcgcga gccctgatg   11580
ctcttcgtcc agatcatcct gatcgacaag accggcttcc atccgagtac gtgctcgctc  11640
gatgcgatgt ttcgcttggt ggtcgaatgg gcaggtagcc ggatcaagcg tatgcagccg  11700
ccgcattgca tcagccatga tggatacttt ctcggcagga gcaaggtgag atgacaggag  11760
atcctgcccc ggcacttcgc ccaatagcag ccagtccctt cccgcttcag tgacaacgtc  11820
gagcacagct gcgcaaggaa cgcccgtcgt ggccagccac gatagccgcg ctgcctcgtc  11880
ctgcagttca ttcagggcac cggacaggtc ggtcttgaca aaaagaaccg ggcgcccctg  11940
cgctgacagc cggaacacgg cggcatcaga gcagccgatt gtctgttgtg cccagtcata  12000
gccgaatagc ctctccaccc aagcggccgg agaacctgcg tgcaatccat cttgttcaac  12060
catggtaatt gtaaatgtaa ttgtaatgtt gtttgttgtt tgttgttgtt ggtaattgtt  12120
gtaaaaatag gagagtgaat atgagactct aattggatac cgaggggaat ttatggaacg  12180
tcagtggagc attttgaca agaaatattt gctagctgat agtgacctta ggcgactttt  12240
gaacgcgcaa taatggtttc tgacgtatgt gcttagctca ttaaactcca gaaaccgcg   12300
gctcagtggc tccttcaacg ttgcggttct gtcagttcca aacgtaaaac ggcttgtccc  12360
gcgtcatcgg cggggggtcat aacgtgactc ccttaattct ccgctcatga tcatccgatg  12420
ggtggattta tcacaaatgg gacccgccgc cgacagaggt gtgatgttag gccaggactt  12480
tgaaatttg cgcaactatc gtatagtggc cgacaaattg acgccgagtt gacagactgc  12540
ctagcatttg agtgaattat gtaagtaat gggctacact gaattggtag ctcaaactgt  12600
tttatt cagtatttat gtatatgagt gtataattttc gcataatct gaagatgaaa  12660
tgggtatctg ggaatggcga aatcaaggca tcgatcgtga agtttctcat ctaagcccc  12720
atttggacgt gaatgtagac acgtcgaaat aaagatttcc gaattagaat aatttgttta  12780
ttgctttcgc ctaaaatac gacggatcgt aatttgtcgt tttatcaaaa tgtactttca  12840
ttttataata acgctgcgga catctacatt tttgaattga aaaaaaattg gtaattactc  12900
tttctttttc tccatattta gttgtgcccc gtagcaaatt gtttgtcaat catctctctc  12960
```

-continued

```
cctcaaactc tcgctctatc tctcgttcgc ttcctctcgc ttttatacaa acacaagtgt    13020
ataaaatttg tttttattat ataaagcgag agaaaattgt ataaatacat atatttttgt    13080
tttcctctgc cagatctc                                                 13098
```

TOMATO PLANTS COMPRISING TRANSGENIC EVENT DEL/ROS1-N

CROSS-REFERENCE TO RELATED APPLICATION

This application claims the benefit of U.S. Provisional Application No. 63/324,405, filed Mar. 28, 2022, which is hereby incorporated herein in its entirety by reference.

REFERENCE TO AN ELECTRONIC SEQUENCE LISTING

The contents of the electronic sequence listing (070314-0012SEQLST.xml; Size: 15,245 bytes; and Date of Creation: Mar. 15, 2023) is herein incorporated by reference in its entirety.

FIELD OF THE INVENTION

The present invention relates to tomato plants, seeds, and fruits comprising transgenic event Del/Ros1-N.

BACKGROUND OF THE INVENTION

Anthocyanins are the red, purple and blue pigments which color many fruits, flowers as well as some vegetables. Dietary anthocyanins are associated with a reduced risk of chronic and degenerative diseases such as cardiovascular disease, obesity and certain cancers. Dietary anthocyanins have been reported to have protective effects against myocardial infarction and coronary heart disease (Cassidy et al., 2013, *Circulation* 127:188-96) as well as ameliorative effects in those already at risk of atherosclerosis (Zhu et al., 2012, *Nutr. Metab. Cardiovasc. Dis.* 23:843-849). People consuming a high fruit and vegetable diet may eat as much as 60 mg of anthocyanins per day, although beneficial effects have involved 5-fold higher anthocyanin consumption levels (>300 mg/day) in human intervention studies (Pojer et al., 2013, *Compr. Rev. Food Sci. Food Saf.* 12:483-508). Consequently, anthocyanin levels in the most commonly eaten fruits and vegetables are probably inadequate to confer optimal benefits. In addition, overall consumption of fruit and vegetables has declined over the last 10 years with only a fraction (approximately 25%) of the U.S. population consuming the recommended 5 daily portions (Potter et al., 2000, "5-A-Day for Better Health. Program evaluation Report," Bethesda, MD: National Institutes of Health, National Cancer Institute, NIH Publication No. 01-4904).

Anthocyanins occur in almost all higher plants, mostly in flowers and fruits, but they are also present in leaves, stems, and some roots and in several familiar fruits and vegetables (Table 1).

TABLE 1

Anthocyanin Contents of Different Foods[1]

| Foodstuff | Anthocyanin Content (mg per 100 g FW[2]) |
|---|---|
| aubergine (eggplant) | 375 |
| blackberry | 83-326 |
| blackcurrant | 130-400 |
| blueberry | 25-497 |
| cherry | 100-400 |
| chokeberry | 200-1000 |
| cranberry | 60-200 |
| elderberry | 450-1375 |
| orange | 8 |
| plum | 1-12 |
| radish | 11-60 |
| raspberry | 10-60 |
| red cabbage | 125-210 |
| red currant | 80-420 |
| red grape | 15-375 |
| red onions | 7-21 |
| red wine | 24-150 |
| rhubarb | 200 |
| strawberry | 15-35 |

[1]Manach et al., 2004, *Am. J. Clin. Nutr.* 79:727-47.
[2]Fresh weight.

While tomato (*Solanum lycopersicum*) plants produce anthocyanins in their leaves, anthocyanins are not synthesized in wild-type tomato fruits, due to mutations in regulatory genes of the anthocyanin biosynthetic pathway (Colanero et al., 2020, *Plant. Physiol.* 182:1841-1853). Some tomato varieties with anthocyanins in the skin of the fruit have been produced by introgression breeding using wild species *Solanum chilense* and *Solanum cheesmaniae* and are currently available to consumers as commercial tomato varieties 'Indigo Rose' and 'Sun Black'. (Mes, 2005, Breeding Tomatoes for Improved Antioxidant Activity. Ph.D. Thesis, Oregon State University, Corvallis, OR. 195 pp.; Mes et al., 2008, *J. Am. Soc. Hort. Sci.* 133:262-269; Gruber, 2017, *Nature* 544: S8-S10). Because the anthocyanins are limited to the skin of the fruit, the anthocyanin contents of whole tomato fruits from these varieties and products made from these tomato fruits such as, for example, tomato juice, is very low. Recently, Blando et al. (2019, *Front. Nutr.* 6:133; doi.org/10.3389/fnut.2019.00133) reported that whole, ripe, purple 'Sun Black' fruit had a total anthocyanin content of 7.1 mg/100 g fresh weight (FW) and 1.2 mg/g dry weight (DW). Blando et al. further reported that anthocyanins were detected in the peel of the 'Sun Black' fruit but not in the flesh and that anthocyanins were not detected either the peel or flesh of red, wild-type tomato fruit. Id.

To achieve high levels of anthocyanins in whole tomato fruit, Butelli et al. (2008, *Nature Biotechnol.* 26:1301-1308) "turned on" the native genes of the anthocyanin biosynthetic pathway in tomato fruit by expressing two transcription factor-encoding genes from snapdragon Delila (Del) and Rosea1 (Ros1) under the control of the E8 fruit-specific promoter from tomato. Anthocyanins were present in both the tomato peel and flesh of the fruit of the transformed tomato lines and at concentrations of anthocyanins in whole tomato fruit ranging from approximately 23 to 280 mg per 100 g fresh weight. Thus, such an approach may be useful in developing commercial tomato lines that produce high levels of anthocyanin in their fruits.

BRIEF SUMMARY OF THE INVENTION

The present invention provides tomato plants and seeds comprising transgenic event Del/Ros1-N. Parts of these tomato plants are also provided including, for example, leaves, pollen, ovules, stems, scions, roots, fruit, and cells. The present invention further comprises food products, including, for example, whole fresh tomato fruits (i.e. tomatoes) and food products made from tomato fruits including, but not limited to tomato juice, ketchup, tomato paste, tomato sauce, whole and/or chopped canned tomatoes, dried tomato fruit and/or fruit parts, tomato puree, and salsa. In a preferred embodiment of the invention, the food product is a tomato juice, particularly a purple tomato juice.

The present invention further provides a tissue culture of regenerable cells of a tomato plant comprising transgenic event Del/Ros1-N. The tissue culture will preferably be capable of regenerating tomato plants capable of expressing all the physiological and morphological characteristics of the starting plant, and of regenerating plants having substantially the same genotype as the starting plant, and particularly transgenic event Del/Ros1-N. The regenerable cells in such tissue cultures may be derived, for example, from embryos, meristems, cotyledons, pollen, leaves, anthers, roots, root tips, pistils, flowers, seeds, fruits, and stalks.

Additionally, the present invention provides methods for producing tomato plants, seeds, and fruit, which methods generally comprise crossing a first parent tomato plant with a second parent tomato plant, wherein at least one of the first or second parent tomato plants is a plant comprising transgenic event Del/Ros1-N. These methods may be further exemplified as methods for preparing hybrid tomato seed or plants, wherein a first tomato plant is crossed with a second tomato plant of a different, distinct genotype to a hybrid that has, as one of its parents, a plant comprising transgenic event Del/Ros1-N. In these methods, crossing will result in the production of seed. The seed production occurs regardless of whether the seed is collected or not. Preferred seeds comprise transgenic event Del/Ros1-N.

In certain embodiments, the present invention provides a method of producing food or feed comprising: (a) obtaining a plant comprising transgenic event Del/Ros1-N, wherein the plant has been cultivated to develop fruit, and (b) harvesting at least one tomato from the plant. The method can further comprise processing the tomato fruit into a food product including, but not limited to tomato juice, ketchup, tomato paste, tomato sauce, whole and/or chopped canned tomatoes, dried tomato fruit and/or fruit parts, tomato puree, and salsa. In one embodiment of the invention, one or more tomato fruits are processed into a tomato juice, preferably a purple tomato juice.

Individual plants in the T1 generation were used for copy number determination by qPCR. One individual plant in the T1 generation of the Del/Ros1N event plant was crossed to 'Moneymaker' to generate a purple-fruited F1 population. One of the F1 plants was selfed, and then a dark purple F2 plant was selfed through 8 generations propagated by single seed descent to develop the stock line "Del/Ros1-N in Moneymaker". The same T1 N plant that was crossed to 'Moneymaker' was also selfed across 6 generations using single seed descent to generate the stock line "Del/Ros1-N in Micro-Tom". Plants from these stock lines were used for characterization of the T-DNA insertion, compositional analyses and segregation analyses.

Figure 2:
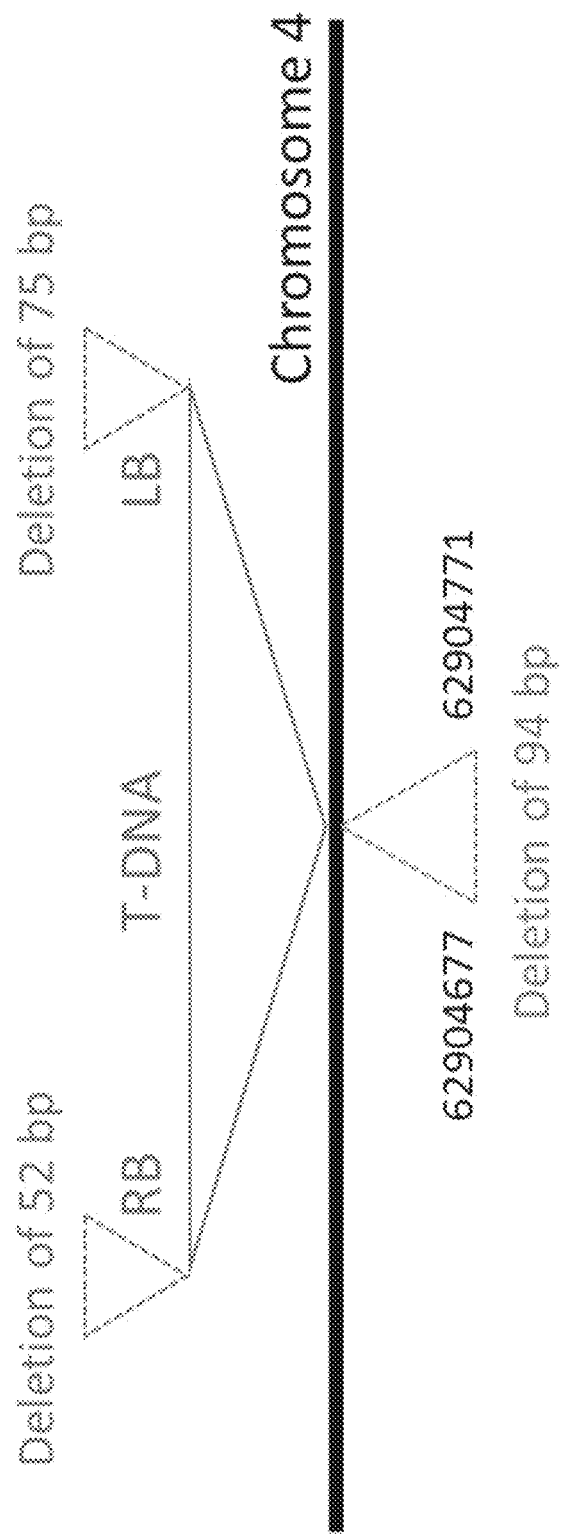

FIG. 2 is a schematic diagram of the insertion site (locus B) of the T-DNA in event Del/Ros1-N in tomato chromosome 4. At the insertion site, there is a 94 bp deletion from the tomato genome between positions 62904677 and 62904771.

Figure 3:
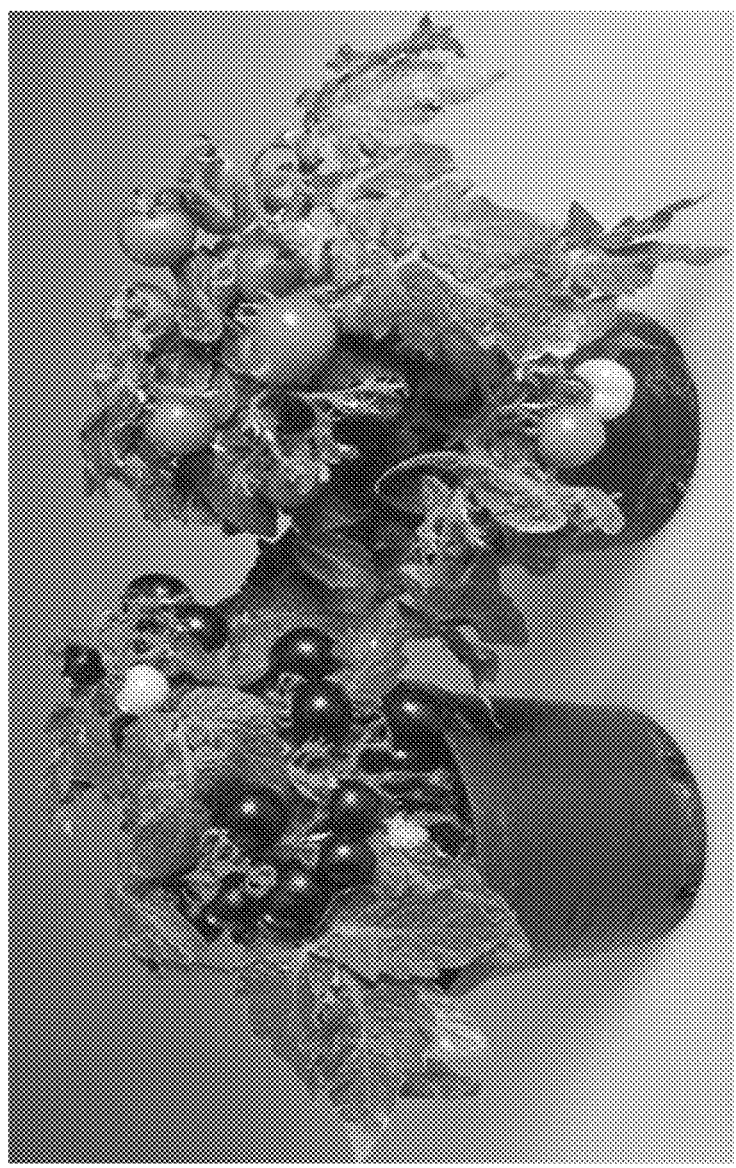

FIG. 3 is a photographic illustration of the growth and fruiting of primary Purple Tomato transformant (left) TO in the Micro-Tom genetic background and wild-type "Micro-Tom" (right).

Figure 4:
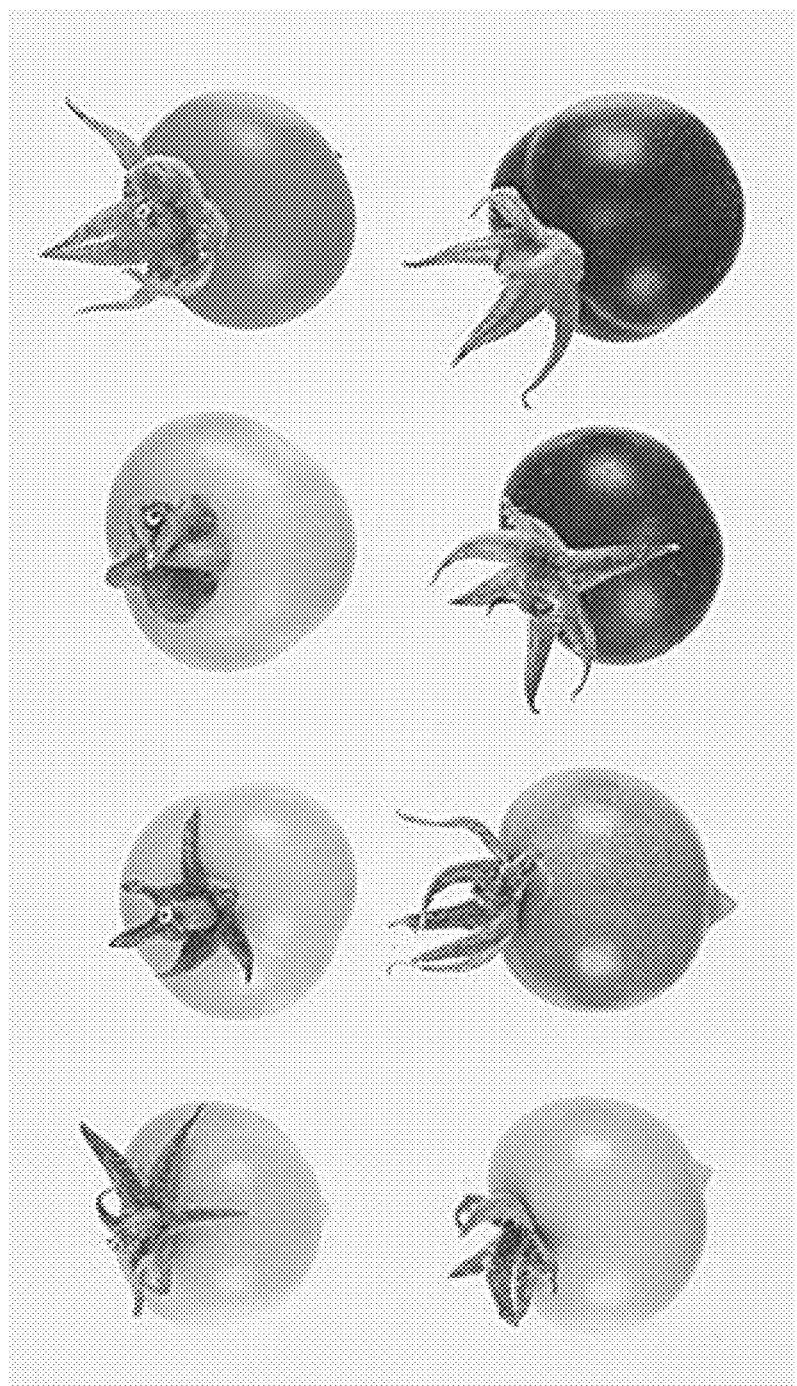

FIG. 4 is a photographic illustration of the phenotype of wild-type (upper row) and Del/Ros1-N(lower row) tomato fruit harvested at the mature green (left), breaker (second left column), breaker plus 2 days (third left column) and red ripe (right) stages.

Figure 5:
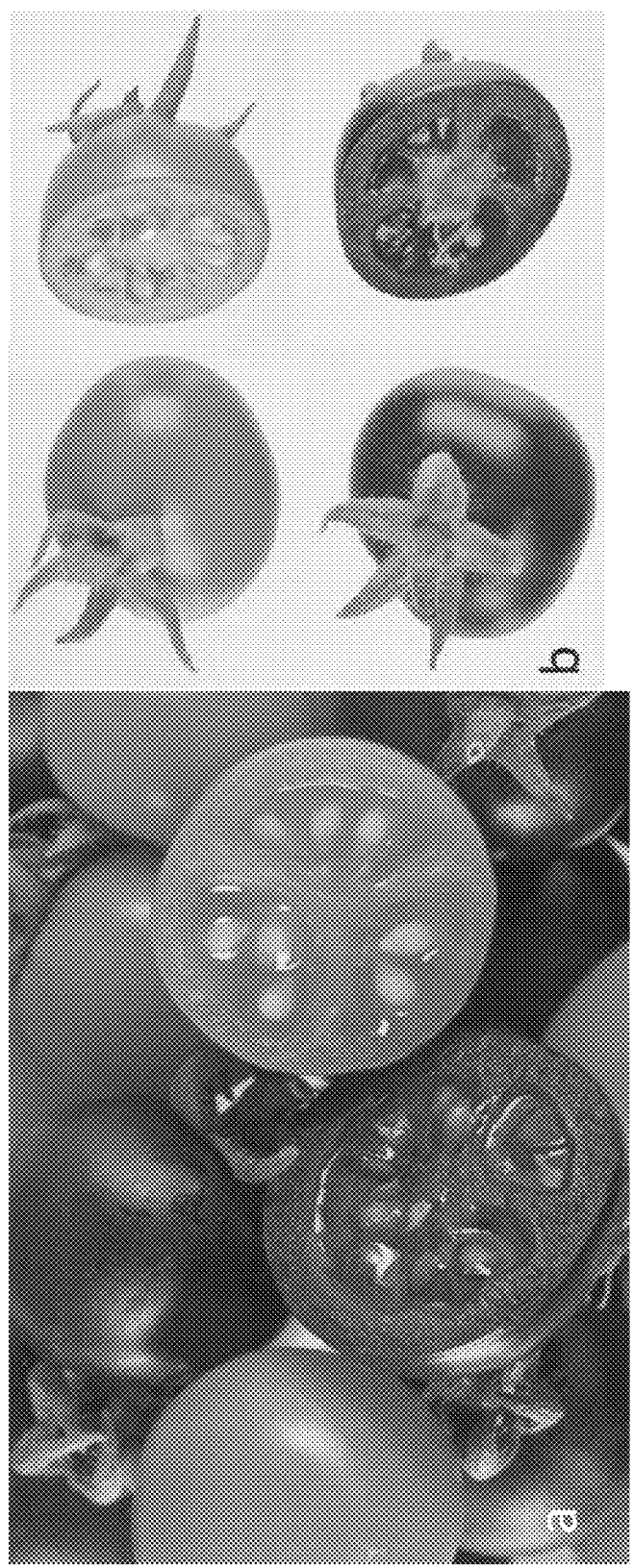

FIG. 5 is a photographic illustration of fruit-specific phenotypes of tomatoes expressing both Del and Ros1 under the control of the E8 promoter. (a) Del/Ros1-N(purple) and wild-type (red) tomatoes. (b) Whole and cross-section of ripe wild-type (top) and Del/Ros1-N(bottom) tomato fruit.

SEQUENCE LISTING

The nucleotide and amino acid sequences listed in the accompanying Sequence Listing are shown using standard letter abbreviations for nucleotide bases, and three-letter code for amino acids. The nucleotide sequences follow the standard convention of beginning at the 5' end of the sequence and proceeding forward (i.e., from left to right in each line) to the 3' end. Only one strand of each nucleotide sequence is shown, but the complementary strand is understood to be included by any reference to the displayed strand. The amino acid sequences follow the standard convention of beginning at the amino terminus of the sequence and proceeding forward (i.e., from left to right in each line) to the carboxy terminus.

SEQ ID NO: 1 sets forth a DNA fragment comprising transgenic event Del/Ros1-N and the flanking wild-type tomato genomic DNA on both sides of the T-DNA insertion site. The locations of the various genetic elements of the DNA fragment that is set forth in SEQ ID NO: 1 are provided in Table 2.

TABLE 2

Annotation of the Del/Ros1 T-DNA Insertion and Flanking Tomato Genomic DNA (SEQ ID NO: 1)[1]

| Nucleotide Position | | |
|---|---|---|
| Start | End | Genetic Element |
| 1 | 332 | Tomato chromosomal DNA ("chr4") position 62904346 . . . 62904677 (Build SL 3.0).<br>94 bp of genomic sequence after position 62904677 have been deleted |
| 333 | 864 | RB region of the T-DNA insert<br>52 bp at the end of the RB region have been deleted (including the RB) |

TABLE 2-continued

Annotation of the Del/Ros1 T-DNA Insertion and
Flanking Tomato Genomic DNA (SEQ ID NO: 1)[1]

| Nucleotide Position | | |
|---|---|---|
| Start | End | Genetic Element |
| 865 | 1502 | CMV (Cauliflower mosaic virus termination region) |
| 1615 | 2277 | ROS (Rosea1 cDNA from snapdragon) |
| 2284 | 4470 | E8p (E8 promoter region from tomato) |
| 4500 | 5227 | CMV (Cauliflower mosaic virus termination region) |
| 5287 | 7221 | DEL (Delila cDNA from snapdragon) |
| 7305 | 9493 | E8p (E8 promoter region from tomato) |
| 10535 | 11242 | Ocs 3 (Octopine synthase termination region) |
| 11269 | 12063 | NPT II (Neomycin phosphotransferase gene conferring resistance to Kanamycin) |
| 12150 | 12329 | NOSp (Nopaline synthase promoter region) |
| 12330 | 12915 | LB region of the T-DNA insert<br>75 bp at the end of the LB region have been deleted (including the LB) |
| 12916 | 13098 | Tomato chromosomal DNA ("chr4") position 62904771 . . . 62904953 (Build SL 3.0) |

[1]A schematic representation and orientation of the Del/Ros1 T-DNA insert and flanking tomato genomic DNA is provided in FIG. 2.

DETAILED DESCRIPTION OF THE INVENTION

The present inventions now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

The invention provides methods and compositions relating to plants, seeds and derivatives of a tomato plant comprising transgenic event Del/Ros1-N. As described hereinbelow, such plants and derivatives are capable of producing tomato fruit comprising high levels of anthocyanins, which are antioxidant compounds with widely recognized human health benefits. Such tomato fruit find use as nutritionally enhanced foods in a fresh form or can be processed into tomato food products comprising high levels of anthocyanins including, for example, tomato juice, ketchup, tomato paste, tomato sauce, whole or chopped canned tomatoes, tomato puree, and salsa. Preferably, such tomato fruits and food products comprise genomic DNA comprising transgenic event Del/Ros1-N.

The tomato plants of the present invention are capable of producing tomato fruit comprising high levels of anthocyanins. A high level of anthocyanins in a tomato fruit of the present invention is typically at least about 50 mg of anthocyanins per 100 g fruit fresh weight for a tomato at the red ripe stage. Preferably, such tomato fruit contains at least about 100 or 200 mg of anthocyanins per 100 g fruit fresh weight. More preferably, such a tomato fruit contains at least about 300, 400, 500, or 600 mg of anthocyanins per 100 g fruit fresh weight.

The tomato fruit of the present invention find us in the production of tomato food products comprising high levels of anthocyanins. In one embodiment of the invention, tomato fruit of the present invention are processed using standard methods to produce a tomato juice comprising a high level of anthocyanins. Such a tomato juice of the present invention typically contains at least about 50 mg of anthocyanins per 100 mL unconcentrated juice. Preferably, such a tomato juice contains at least about 100 or 200 mg of anthocyanins per 100 mL unconcentrated juice without the addition of anthocyanins. More preferably, such a tomato juice contains at least about 300, 400, 500, or 600 mg of anthocyanins 100 mL unconcentrated juice without the addition of anthocyanins.

The invention further provides methods for producing a food product from one or more tomato fruits of the present invention or part or parts thereof of the tomato fruit(s). The methods comprise processing a whole tomato fruit, particularly a ripe tomato fruit, or part or parts thereof, whereby a food product is produced, particular a food product comprising a high level of anthocyanins without the addition of anthocyanins as compared to a food product produced by the same method using a red, wild-type tomato fruit or part or parts thereof. Preferably, such a food product comprises an anthocyanin content that is 2-fold, 3-fold, 4-fold, 5-fold, 10-fold or greater than the anthocyanin content of the same food product produced from red, wild-type tomato fruit or part or parts thereof. Such processing can comprise any known method of processing tomato fruit to make a food product, including, but not limited to, crushing, extracting, chopping, pressing, macerating, mashing, blending, pureeing, peeling, heating, chilling, steaming, filtering, centrifuging, and/or concentrating (i.e. removing water).

Such methods for producing a food product include, for example, methods for producing a tomato juice, particularly a tomato juice comprising a high level of anthocyanins. The methods for producing a tomato juice comprising extracting juice from a tomato fruit of the present invention, whereby a tomato juice is produced. Preferably, the tomato juice comprises an anthocyanin content that is 2-fold, 3-fold, 4-fold, 5-fold, 10-fold or greater than a juice produced by the same method using a red, wild-type tomato fruit or part or parts thereof. Extracting the tomato juice can comprise any known method of extracting tomato juice from a tomato fruit or part thereof, including, but not limited to, crushing, chopping, pressing, macerating, mashing, blending, pureeing, peeling, heating, steaming, chilling, freezing, filtering, centrifuging, and/or concentrating. Preferably, a tomato juice produced by the present invention contains at least about 100 or 200 mg of anthocyanins per 100 mL unconcentrated juice without the addition of anthocyanins. More preferably, such a tomato juice contains at least about 300, 400, 500, or 600 mg of anthocyanins 100 mL unconcentrated juice without the addition of anthocyanins.

Transgenic event Del/Ros1-N has been introgressed into several tomato varieties including both fresh market and processing tomato varieties and shown to produce tomato fruit with high-levels of anthocyanins. The varieties are 'Micro-Tom', 'Moneymaker', 'Ailsa Craig', 'VF36', 'Ohio 8423', and 'Maglia Rosa'. Thus, it is expected that transgenic event Del/Ros1-N can be introduced into any tomato variety or line to make improved tomato varieties or lines that produce tomato fruits, preferably purple tomato fruits, comprising high levels of anthocyanins.

Preferably, the tomato plants and seeds of the invention are of the species *Solanum lycopersicum* (formerly known as *Lycopersicon esculentum*). However, the present invention includes, but is not limited to, plants comprising transgenic event Del/Ros1-N that are of species with the genus *Solanum*, preferably within the subgenus *Lycopersicon*, other than *Solanum lycopersicum*. It is recognized that there are methods known in the art for introducing a transgenic event, such as, for example, transgenic event Del/Ros1-N, from one plant species to another closely related plant species and that the use of any such methods is encompassed by the present invention. Such methods comprise, for example, cross-pollination, and can optionally further comprise embryo rescue. Closely related plant species include, for example, two species within the same family (e.g. Solanaceae), preferably two species within the same subfamily (e.g. Solanoideae), more preferably two species within the same tribe (e.g. Solancae), even more preferably two species within the same genus (e.g. *Solanum*), and most preferably two species within the same subgenus (e.g. *Lycopersicon*).

The present invention is drawn to tomato plants comprising transgenic event Del/Ros1-N. A transgenic "event" is produced by the transformation of plant cells with at least one heterologous DNA construct, including a nucleic acid expression cassette that comprises a transgene of interest, the regeneration of a population of plants resulting from the insertion of the transgene into the genome of the plant, and selection of a particular plant characterized by insertion into a particular genome location. An event is characterized phenotypically by the expression of the transgene. At the genetic level, an event is part of the genetic makeup of a plant. The term "event" also refers to progeny produced by a sexual outcross between the transformant and another variety that include the heterologous DNA. Even after repeated back-crossing to a recurrent parent, the inserted DNA and flanking DNA from the transformed parent is present in the progeny of the cross at the same chromosomal location. The term "event" also refers to DNA from the original transformant comprising the inserted DNA and flanking sequence immediately adjacent to the inserted DNA that would be expected to be transferred to a progeny that receives inserted DNA including the transgene of interest as the result of a sexual cross of one parental line that includes the inserted DNA (e.g., the original transformant and progeny resulting from selfing) and a parental line that does not contain the inserted DNA.

Definitions of some additional terms used herein include, but are not limited to, the following definitions:

"Backcrossing" is a process in which a breeder repeatedly crosses hybrid progeny, for example a first generation hybrid (F1), back to one of the parents of the hybrid progeny. Backcrossing can be used to introduce one or more single locus conversions from one genetic background into another.

"Crossing" is the mating of two parent plants.

"Cross-pollination" is the fertilization by the union of two gametes from different plants.

A "diploid" is a cell or organism having two sets of chromosomes.

"Emasculate" means to remove of plant male sex organs or the inactivation of the organs with a cytoplasmic or nuclear genetic factor or a chemical agent conferring male sterility.

"Enzymes" are molecules which can act as catalysts in biological reactions.

An "F1 Hybrid" is the first generation progeny of the cross of two nonisogenic plants.

A "genotype" is the genetic constitution of a cell or organism.

A "haploid" is a cell or organism having one set of the two sets of chromosomes in a diploid.

"Linkage" is a phenomenon wherein alleles on the same chromosome tend to segregate together more often than expected by chance if their transmission was independent.

A "Marker" is a readily detectable phenotype, preferably inherited in codominant fashion (both alleles at a locus in a diploid heterozygote are readily detectable), with no environmental variance component, i.e., heritability of 1.

A "phenotype" is the detectable characteristics of a cell or organism, which characteristics are the manifestation of gene expression.

"Quantitative Trait Loci (QTL)" refer to genetic loci that control to some degree numerically representable traits that are usually continuously distributed.

"Regeneration" is the development of a plant from tissue culture.

"Self-pollination" is the transfer of pollen from the anther to the stigma of the same plant.

A "Single Locus Converted (Conversion) Plant" is a plant which is developed by a plant breeding technique called backcrossing, wherein essentially all of the morphological and physiological characteristics of a tomato variety are recovered in addition to the characteristics of the single locus transferred into the variety via the backcrossing technique and/or by genetic transformation.

"Substantially Equivalent" is a characteristic that, when compared, does not show a statistically significant difference (e.g., p=0.05) from the mean.

"Tissue Culture" is a composition comprising isolated cells of the same or a different type or a collection of such cells organized into parts of a plant.

A "transgene" is a genetic locus comprising a sequence which has been introduced into the genome of a plant by transformation.

Additional terms concerning the present invention are defined elsewhere herein above and below.

The tomato plants of the present invention are derived from a single transgenic event comprising the insertion of two copies of a T-DNA construct containing an E8 promoter::Del gene and an E8 promoter::Ros gene into the genome of a 'Micro-Tom' tomato plant. Analysis of the primary transformants (T1) indicated that there were two copies inserted into two unlinked loci, referred to herein as locus A and locus B. For the locus B insertion, the T-DNA insertion occurred on chromosome 4 at position 62904771. For the locus A insertion, the T-DNA insertion occurred on chromosome 2 at position 10442077. The T1 plant was selfed across 6 generations using single seed descent to generate the stock line "Del/Ros1-N in Micro-Tom". Locus A was lost through the subsequent generations through segregation. Thus, the tomato plants of the present invention comprising transgenic event Del/Ros1-N possess a single copy of the T-DNA construct containing the E8 promoter::Del gene and the E8 promoter::Ros gene at locus B.

One aspect of the current invention concerns methods for producing new tomato lines and hybrids comprising transgenic event Del/Ros1-N and that are capable of producing purple fruit having high levels of anthocyanins. The methods involve crossing a first tomato plant comprising transgenic event Del/Ros-N with a second tomato plant lacking transgenic event Del/Ros1-N. The first plant can be homozygous or hemizygous for transgenic event Del/Ros1-N. However, in preferred embodiments the first plant is homozygous for transgenic event Del/Ros1-N whereby all F1 progeny of the crossing will comprise transgenic event Del/Ros1-N. If the first plant is hemizygous for transgenic event Del/Ros1-N, then the method can comprise the optional step of selecting for the presence of the transgenic event Del/Ros1-N using, for example, a PCR approach to identify progeny plants comprising transgenic event Del/Ros1-N.

The development of new varieties using one or more starting lines is well known in the art. In accordance with the invention, novel varieties may be created by crossing a tomato plant comprising transgenic event Del/Ros1-N with a second tomato plant followed by multiple generations of breeding according to methods well known in the art and/or described elsewhere herein. New varieties may be created by crossing with any second plant. In selecting such a second plant to cross for the purpose of developing novel lines, it may be desired to choose those plants which either themselves exhibit one or more selected desirable characteristics or which exhibit the desired characteristic(s) when in hybrid combination. Once initial crosses have been made, inbreeding and selection take place to produce new varieties. For development of a uniform line, often five or more generations of selfing and selection are involved.

Uniform lines of new varieties may also be developed by way of double-haploids. This technique allows the creation of true breeding lines without the need for multiple generations of selfing and selection. In this manner true breeding lines can be produced in as little as one generation. Haploid embryos may be produced from microspores, pollen, anther cultures, or ovary cultures. The haploid embryos may then be doubled autonomously, or by chemical treatments (e.g. colchicine treatment). Alternatively, haploid embryos may be grown into haploid plants and treated to induce chromosome doubling. In either case, fertile homozygous plants are obtained. In accordance with the invention, any of such techniques may be used in connection with a plant of the invention and progeny thereof to achieve a homozygous line.

Backcrossing can also be used to improve an inbred plant. Backcrossing transfers a specific desirable trait from one inbred or non-inbred source to an inbred that lacks that trait. This can be accomplished, for example, by first crossing a superior inbred (A) (recurrent parent) to a donor inbred (non-recurrent parent), which carries the appropriate locus or loci for the trait in question. The progeny of this cross are then mated back to the superior recurrent parent (A) followed by selection in the resultant progeny for the desired trait to be transferred from the non-recurrent parent. After five or more backcross generations with selection for the desired trait, the progeny have the characteristic being transferred, but are like the superior parent for most or almost all other loci. The last backcross generation would be selfed to give pure breeding progeny for the trait being transferred.

The plants of the present invention are particularly well suited for the development of new lines that are capable of producing purple fruit having high levels of anthocyanins. In selecting a second plant to cross with a first plant comprising transgenic event Del/Ros1-N for the purpose of developing novel tomato lines, it will typically be preferred to choose those plants which either themselves exhibit one or more selected desirable characteristics or which exhibit the desired characteristic(s) when in hybrid combination. Examples of desirable traits may include, in specific embodiments, high seed yield, high seed germination, seedling vigor, high fruit yield, disease tolerance or resistance, and adaptability for soil and climate conditions. Consumer-driven traits, such as a fruit shape, color, texture, and taste are other examples of traits that may be incorporated into new lines of tomato plants developed by this invention.

In certain aspects of the invention, plants described herein are provided modified to include at least a first desired heritable trait. Such plants may, in one embodiment, be developed by a plant breeding technique called backcrossing, wherein essentially all the morphological and physiological characteristics of a variety are recovered in addition to a genetic locus transferred into the plant via the backcrossing technique. The term single locus converted plant as used herein refers to those tomato plants which are developed by a plant breeding technique called backcrossing, wherein essentially all the morphological and physiological characteristics of a variety are recovered in addition to the single locus transferred into the variety via the backcrossing technique. By essentially all the morphological and physiological characteristics, it is meant that the characteristics of a plant are recovered that are otherwise present when compared in the same environment, other than an occasional variant trait that might arise during backcrossing or direct introduction of a transgene.

Backcrossing methods can be used with the present invention to improve or introduce a characteristic into the present variety. For the present invention, the parental tomato plant which contributes transgenic event Del/Ros1-N is termed the nonrecurrent or donor parent. This terminology refers to the fact that the nonrecurrent parent is used one time in the backcross protocol and therefore does not recur. The parental tomato plant to which transgenic event Del/Ros1-N from the nonrecurrent parent are transferred is known as the recurrent parent as it is used for several rounds in the backcrossing protocol.

In a typical backcross protocol, the original variety of interest (recurrent parent) is crossed to a second variety (nonrecurrent parent) that carries the single locus of interest (e.g. transgenic event Del/Ros1-N) to be transferred. The resulting progeny from this cross are then crossed again to the recurrent parent and the process is repeated until a tomato plant is obtained wherein essentially all of the morphological and physiological characteristics of the recurrent parent are recovered in the converted plant, in addition to the single transferred locus from the nonrecurrent parent.

The selection of a suitable recurrent parent is an important step for a successful backcrossing procedure. The goal of a backcross protocol is to alter or substitute a single trait or characteristic in the original variety. To accomplish this, a single locus of the recurrent variety is modified or substituted with the desired locus from the nonrecurrent parent, while retaining essentially all of the rest of the desired genetic, and therefore the desired physiological and morphological constitution of the original variety. The choice of the particular nonrecurrent parent will depend on the purpose of the backcross; one of the major purposes is to add some commercially desirable trait to the plant. The exact backcrossing protocol will depend on the characteristic or trait being altered and the genetic distance between the recurrent and nonrecurrent parents. Although backcrossing methods are simplified when the characteristic being transferred is a dominant allele, a recessive allele, or an additive allele (between recessive and dominant), may also be transferred. In this instance it may be necessary to introduce a test of the progeny to determine if the desired characteristic has been successfully transferred.

In one embodiment, progeny tomato plants of a backcross in which a plant described herein is the recurrent parent comprise (i) the desired trait from the non-recurrent parent and (ii) all the physiological and morphological characteristics of tomato the recurrent parent as determined at the 5% significance level when grown in the same environmental conditions.

New varieties can also be developed from more than two parents. The technique, known as modified backcrossing, uses different recurrent parents during the backcrossing. Modified backcrossing may be used to replace the original recurrent parent with a variety having certain more desirable characteristics or multiple parents may be used to obtain different desirable characteristics from each.

Many single locus traits have been identified that are not regularly selected for in the development of a new inbred but that can be improved by backcrossing techniques. Single locus traits may or may not be transgenic; examples of these traits include, but are not limited to, herbicide resistance, resistance to bacterial, fungal, or viral disease, insect resistance, modified fatty acid or carbohydrate metabolism, and altered nutritional quality. These comprise genes generally inherited through the nucleus.

Direct selection may be applied where the single locus acts as a dominant trait. For this selection process, the progeny of the initial cross are assayed for the trait and/or the presence of the corresponding gene prior to the backcrossing. Selection eliminates any plants that do not have the desired gene and resistance trait, and only those plants that have the trait are used in the subsequent backcross. This process is then repeated for all additional backcross generations.

Selection of tomato plants for breeding is not necessarily dependent on the phenotype of a plant and instead can be based on genetic investigations. For example, one can utilize a suitable genetic marker which is closely genetically linked to a trait of interest. One of these markers can be used to identify the presence or absence of a trait in the offspring of a particular cross, and can be used in selection of progeny for continued breeding. This technique is commonly referred to as marker assisted selection. Any other type of genetic marker or other assay which is able to identify the relative presence or absence of a trait of interest in a plant can also be useful for breeding purposes. Procedures for marker assisted selection are well known in the art. Such methods will be of particular utility in the case of recessive traits and variable phenotypes, or where conventional assays may be more expensive, time consuming or otherwise disadvantageous. Types of genetic markers which could be used in accordance with the invention include, but are not necessarily limited to, Simple Sequence Length Polymorphisms (SSLPs) (Williams et al., 1990), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858, specifically incorporated herein by reference in its entirety), and Single Nucleotide Polymorphisms (SNPs).

Typically, the tomato plants of the present invention are grown outdoors in agricultural fields or other outdoor fields or gardens, but the methods of the invention can also be used with tomato plants grown under greenhouse conditions or under other indoor or controlled-environment conditions. The tomato plants are allowed to grow and produce mature tomato fruit and then the fruit are harvested from the plants.

As used herein control tomato plants are tomato plants lacking transgenic event Del/Ros1-N. Preferably, such control tomato plants are of the same or essentially the same genotype as the tomato plants comprising transgenic event Del/Ros1-N, except that the control tomato plants lack transgenic event Del/Ros1-N.

As used herein, a wild-type tomato plant is a non-transgenic tomato (*Solanum lycopersicum*) plant. Preferably, such a wild-type tomato plant comprises a genome that has not been modified using a genome editing technique. A tomato fruit produced by a wild-type tomato plant of the present invention is referred to herein as a wild-type tomato fruit or a wild-type tomato.

The tomato plants of the present invention additional comprise grafted tomato plants. Such grafted tomato plants can be produced, for example, by grafting a stem or scion excised from a tomato plant comprising transgenic event Del/Ros1-N on a tomato rootstock, particularly a rootstock from a tomato plant lacking transgenic event Del/Ros1-N. Such grafted plants find use when the rootstock provides a particular trait of interest (e.g. resistance against nematodes and/or other root diseases) that is not present in the stem or scion. Typically, a tomato rootstock comprises both roots and stem tissue and is produced by removing most of the above-ground portion of a tomato plant, particularly a young tomato plant (i.e. a seedling), but retaining a small portion of the main stem, onto to which a tomato stem comprising a meristem can be grafted.

A deposit of at least 625 tomato seeds comprising transgenic event Del/Ros-N disclosed above and recited in the claims, was made with NCIMB Ltd. (Ferguson Building, Craibstone Estate, Bucksburn, Aberdeen, AB21 9YA Scotland), and the deposit was assigned Accession Number NCIMB 43839. The deposit date is Aug. 9, 2021. This deposit will be maintained under the terms of the Budapest Treaty on the International Recognition of the Deposit of Microorganisms for the Purposes of Patent Procedure. This deposit was made merely as a convenience for those of skill in the art and is not an admission that a deposit is required under 35 U.S.C. § 112. Upon issuance of a patent, all restrictions upon the deposits will be removed, and the deposits are intended to meet all the requirements of 37

C.F.R. §§ 1.801-1.809. The deposits will be maintained in the depository for a period of 30 years, or 5 years after the last request, or for the effective life of the patent, whichever is longer, and will be replaced if necessary during that period. As noted above the tomato plants of the present invention comprising transgenic event Del/Ros1-N possess a single copy of the T-DNA construct containing the E8 promoter::Del gene and the E8 promoter::Ros gene at locus B as do the seeds deposited under Accession Number NCIMB 43839. The deposited seeds comprise transgenic event Del/Ros1-N in the Micro-Tom genetic background.

EXAMPLES

Example 1: Development of Tomato Lines Comprising Del/Ros1-N

Figure 1:
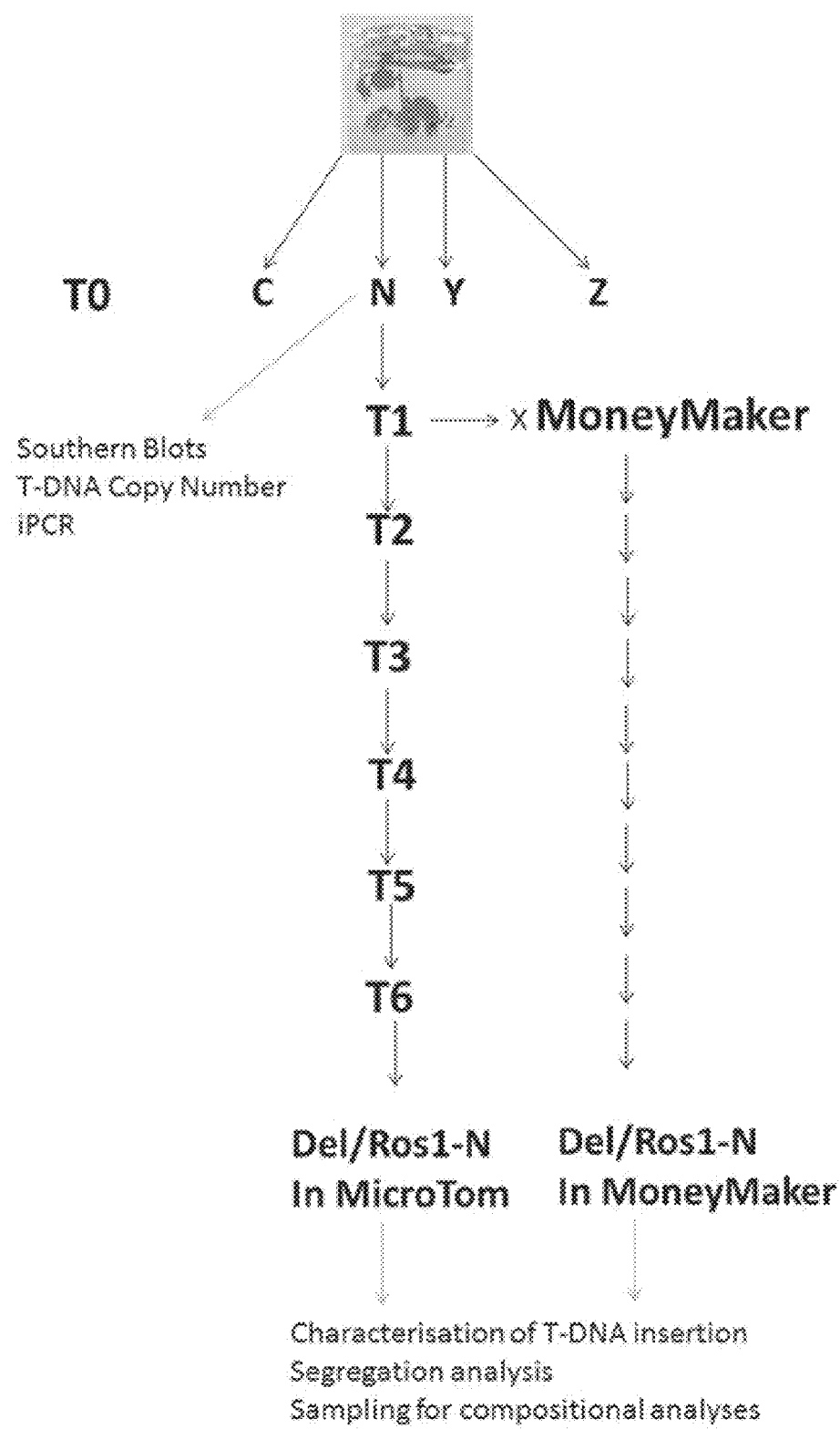
FIG. 1 shows the breeding scheme for event Del/Ros1-N in 'Micro-Tom' and 'Moneymaker' genetic backgrounds. Four primary transformants carrying the pDEL.ROS1 vector were generated (lines C. N. Y, and Z). These were analyzed by Southern blot to determine the T-DNA copy number using the Ros1 cDNA as a probe (data not shown).

Transgenic event Del/Ros1-N was produced by *Agrobacterium*-mediated transformation of tomato (*Solanum lycopersicum*) cultivar 'Micro-Tom' as reported in Butelli et al. (2008, *Nature Biotechnol.* 26:1301-1308). After the molecular analysis of the T0 and T1 plants, purple-fruited lines were selected in the T2 and then in the T3 generation, by single seed descent. One purple-fruited plant from the T1 generation was outcrossed to Moneymaker (a red globe tomato variety) and the purple fruited F1 plants were selfed through 9 generations to generate homozygous globe-fruited line with high anthocyanin, purple fruit (FIG. 1). The same plant used as the parent in this line was selfed until it bred true for purple fruit in the Micro-Tom background (5 further generations) and was then maintained as a stock line (FIG. 1).

Example 2: Genetic Stability of T-DNA Inserts in Tomato Lines Comprising Del/Ros1-N The purple fruit phenotype was stable over more than 6 generations and transferred by cross fertilization into more than 6 different genetic backgrounds confirming the stability of the transgenes and their phenotype. DNA from plants with purple fruit of the T6 generation of Del/Ros1-N in Micro-Tom and from plants with purple fruit from an outcross of Del/Ros1-N (T1)×Moneymaker (selfed over 9 generations) were analyzed for T-DNA insertions at locus A and locus B. The T-DNA insertion at locus A was not detected in either of these derived stock lines indicating that it had segregated away during the selfing that generated the lines. This was confirmed by attempts to amplify the T-DNA insertion using primers from the left and right borders of the T-DNA and the flanking sites at locus A. Using primers from the sequences flanking the original insertion at locus A, a wild-type fragment of DNA of 1.25 kb was amplified from both stock lines as well as from the control WT DNA from Micro-Tom. Sequencing of this fragment of DNA confirmed that it was the wild-type sequence from Micro-Tom with no footprints and that the T-DNA insertion at locus A had segregated away rather than been lost by recombination.

The original Del/Ros1-N transformation event contained two distinct T-DNA insertions, one (insert A) on chromosome 2 and a second (insert B) on chromosome 4. Following Mendelian segregation, tomato plants exhibiting a stable purple fruit phenotype and containing only the transgenic insert B were retained.

The T-DNA insertion from locus B was detected in both Micro-Tom and Moneymaker derived stock lines (data not shown). Comparison of the sequences flanking the left and right borders of the T-DNA between T1 vs T6 Micro-Tom plants and F9 Moneymaker vs T6 Micro-Tom plants confirmed the stability of the locus B insertion in the tomato genome across generations and genetic backgrounds at position 62904771 on chromosome 4 (FIG. 2).

Example 3: Genetic Stability of the Purple Tomato Phenotype Over Multiple Generations in Tomato Lines Comprising Del/Ros1-N Purple Tomato stock plant(s) containing the Del/Ros1-N transformation event at locus B have been monitored in Micro-Tom for greater than 6 generations. The purple tomato trait has been introgressed into other tomato varieties such as 'Ailsa Craig', 'Lucinda', 'VF36', and 'Maglia Rosa' and into an industrial processing tomato variety ('Ohio 8423') for the medium scale production of purple tomato juice.

During the vegetative stage, the growth and development of Del/Ros1-N transgenic tomato plants in the Micro-Tom and Moneymaker genetic backgrounds was indistinguishable from controls (FIG. 3). Because the transcription factors were expressed under the control of a fruit-specific promoter which is active only from the point of fruit ripening (breaker stage), no impact of expressing Del and Ros1 was observed on plant growth, flowering or fruit set, and consequently, no yield penalty was observed in comparisons of transformants to wild-type plants (FIGS. 3-5). Stems and leaves showed no elevated anthocyanin accumulation.

Transgenic fruit exhibited visible signs of purple pigmentation only at the end of the mature green stage, which matched the activity of the fruit-specific E8 promoter (Kneissl & Deikman, 1996, *Plant Physiol.* 112:537-547) used to drive the expression of the Del and Ros1 genes. Pigmentation intensified rapidly in the few days after breaker, initially associated with the vascular tissue but quickly extending to peel, pericarp and inner flesh (FIGS. 4-5).

The purple phenotype was inherited in a Mendelian fashion in all tomato genetic backgrounds. For example, data for the F2 of Del/Ros1-N crossed to VF36 are shown in Table 3.

TABLE 3

Genotypic and Phenotypic Segregation of nptII, Kanamycin Resistance, and the Del/Ros1Phenotype in the F2 Generation of a Del/Ros1-N[1] × VF36 Cross

| Presence of nptII Gene | | Resistance to Kanamycin | | Color of Tomato Fruit | |
|---|---|---|---|---|---|
| Present | 16 | Resistant | 16 | Purple | 16 |
| Absent | 4 | Sensitive | 4 | Red | 4 |

[1]In the Moneymaker background, F9.

The article "a" and "an" are used herein to refer to one or more than one (i.e., to at least one) of the grammatical object of the article. By way of example, "an element" means one or more element.

Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps.

All publications and patent applications mentioned in the specification are indicative of the level of those skilled in the art to which this invention pertains. All publications and U.S. Pat. applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

The invention claimed is:

1. A tomato plant or seed comprising in its genome at least one copy of transgenic event Del/Ros1-N, wherein a representative sample of seed comprising the transgenic event has been deposited under Accession Number NCIMB 43839, and wherein the tomato plant or seed comprising transgenic event Del/Ros1-N comprises in its genome the nucleotide sequence set forth in SEQ ID NO: 1.

2. A progeny tomato plant of the tomato plant of claim 1, wherein the progeny tomato plant is the progeny plant of any generation of the tomato plant and comprises in its genome the nucleotide sequence set forth in SEQ ID NO: 1.

3. The tomato plant or seed of claim 1, wherein the tomato plant or seed is an inbred tomato plant or seed.

4. The tomato plant or seed of claim 1, wherein the tomato plant or seed is a hybrid tomato plant or seed and the hybrid tomato plant or seed comprises in its genome the nucleotide sequence set forth in SEQ ID NO: 1.

5. A plant part of the tomato plant of claim 1, wherein the plant part comprising transgenic event Del/Ros1-N comprises in its genome the nucleotide sequence set forth in SEQ ID NO: 1.

6. The plant part of claim 5, wherein the part is selected from the group consisting of a leaf, a stem, a root, a scion, a rootstock, an ovule, pollen, a fruit, and a cell.

7. A grafted tomato plant comprising the stem, scion, or rootstock of claim 6.

8. A food product produced from the fruit of claim 6 or a part or parts of the fruit, wherein the food product comprises DNA comprising the nucleotide sequence set forth in SEQ ID NO: 1.

9. The food product of claim 8, wherein the food product is selected from the group consisting of ketchup, a tomato juice, a tomato paste, a tomato sauce, whole or chopped canned tomatoes, a dried tomato or part thereof, a tomato puree, and salsa.

10. A tissue culture of regenerable cells of the plant of claim 1, wherein the tissue culture of regenerable cells comprising transgenic event Del/Ros1-N comprises in its genome the nucleotide sequence set forth in SEQ ID NO: 1.

11. A tomato plant regenerated from the tissue culture of claim 10, wherein the regenerated tomato plant comprises the transgenic event.

12. A tomato juice produced from a tomato fruit comprising transgenic event Del/Ros1-N, wherein a representative sample of tomato seed comprising the transgenic event has been deposited under Accession Number NCIMB 43839, and wherein the tomato juice comprises DNA comprising the nucleotide sequence set forth in SEQ ID NO: 1.

13. A method of vegetatively propagating a tomato plant comprising the steps of:
(a) collecting tissue capable of being propagated from the tomato plant of claim 1;
(b) cultivating said tissue to obtain proliferated shoots; and
(c) rooting said proliferated shoots to obtain vegetatively propagated tomato plants comprising roots and shoots, wherein the vegetatively propagated tomato plants comprise in their genomes the nucleotide sequence set forth in SEQ ID NO: 1.

14. A method of introducing transgenic event Del/Ros1-N into a tomato line comprising crossing first a tomato plant comprising transgenic event Del/Ros1-N with a second tomato plant lacking the transgenic event, wherein the first tomato plant is the tomato plant of claim 1, whereby an F1 seed comprising in its genome the nucleotide sequence set forth in SEQ ID NO: 1 is produced.

15. A tomato plant produced by growing the F1 seed of claim 14 so as to produce a tomato plant comprising in its genome the nucleotide sequence set forth in SEQ ID NO: 1.

16. A method of producing a tomato seed comprising crossing the tomato plant of claim 1 with itself or a second tomato plant and allowing seed to form, wherein the seed comprises in its genome the nucleotide sequence set forth in SEQ ID NO: 1.

17. A method of producing a tomato fruit comprising:
(a) obtaining the plant according to claim 1, wherein the plant has been cultivated to develop fruit; and
(b) harvesting a tomato fruit from the plant.

18. A method of producing a food product from a tomato fruit, the method comprising processing a whole, tomato fruit comprising tomato comprising transgenic event Del/Ros1-N, or at least one part the fruit, so as to produce a food product, wherein a representative sample of tomato seed comprising the transgenic event has been deposited under Accession Number NCIMB 43839, wherein the tomato fruit comprising transgenic event Del/Ros1-N comprises in its genome the nucleotide sequence set forth in SEQ ID NO: 1.

19. The method of claim 18, wherein the food product comprises an anthocyanin content that is at least two-fold greater than a food product produced from a red, wild-type tomato fruit using the method.

20. The method of claim 18, wherein the food product is selected from the group consisting of tomato juice, ketchup, tomato paste, tomato sauce, whole and/or chopped canned tomatoes, dried tomato fruit and/or fruit parts, tomato puree, and salsa.

* * * * *